United States Patent
Claessens et al.

(10) Patent No.: US 11,172,623 B2
(45) Date of Patent: Nov. 16, 2021

(54) LAYERED PRODUCT COMPRISING SUPERABSORBENT POLYMER

(71) Applicant: WATERDRAGER HOLDING B.V., Zoetermeer (NL)

(72) Inventors: Marco Johannes Cornelis Marie Claessens, Munstergeleen (NL); Thomas Roeling, Zoetermeer (NL)

(73) Assignee: WATERDRAGER HOLDING B.V., Zoetermeer (NL)

( * ) Notice: Subject to any disclaimer, the term of this patent is extended or adjusted under 35 U.S.C. 154(b) by 232 days.

(21) Appl. No.: 16/075,179

(22) PCT Filed: Feb. 2, 2017

(86) PCT No.: PCT/EP2017/052268
§ 371 (c)(1),
(2) Date: Aug. 3, 2018

(87) PCT Pub. No.: WO2017/134171
PCT Pub. Date: Aug. 10, 2017

(65) Prior Publication Data
US 2019/0037785 A1 Feb. 7, 2019

(30) Foreign Application Priority Data
Feb. 3, 2016 (NL) ..................... 2016217

(51) Int. Cl.
*B32B 5/06* (2006.01)
*A01G 24/35* (2018.01)
(Continued)

(52) U.S. Cl.
CPC ............. *A01G 24/35* (2018.02); *A01G 24/20* (2018.02); *A01G 24/46* (2018.02); *A61F 13/53* (2013.01);
(Continued)

(58) Field of Classification Search
CPC ....................................................... B32B 5/06
See application file for complete search history.

(56) References Cited

U.S. PATENT DOCUMENTS 3,695,270 A * 10/1972 Dostal ................. A61F 13/2071
604/375
4,495,082 A * 1/1985 Mita ....................... A61F 13/53
252/194
(Continued)

FOREIGN PATENT DOCUMENTS

BE 1007122 A3 4/1995
EP 0 160 569 A2 11/1985
(Continued)

OTHER PUBLICATIONS

Communication pursuant to Rule 114(2) EPC from the EPO family member application EP17702639.0, filed Mar. 2, 2020, pp. 1-10.
(Continued)

*Primary Examiner* — Andrew T Piziali
(74) *Attorney, Agent, or Firm* — Hudak, Shunk & Farine Co. LPA

(57) ABSTRACT

A layered product including at least one natural fiber layer including a web of natural fibers and at least one SAP layer including a non-woven substrate including a thermoplastic polymer fibers and a superabsorbent polymer adhered to thermoplastic polymer fibers, wherein the non-woven substrate is a high loft fabric, for example an airlaid or spunlaid non-woven, and wherein the natural fiber layer and the SAP layer are connected to each other by needle punching, stitch bonding or using an adhesive. A process to prepare the layered product and the use of the layered product in for example horticulture.

13 Claims, 2 Drawing Sheets

(51) Int. Cl.
  B32B 5/26      (2006.01)
  C08F 220/06    (2006.01)
  C09J 4/00      (2006.01)
  A61F 13/53     (2006.01)
  B32B 21/10     (2006.01)
  B32B 5/08      (2006.01)
  B32B 7/12      (2006.01)
  A01G 24/20     (2018.01)
  A01G 24/46     (2018.01)
  B32B 5/02      (2006.01)

(52) U.S. Cl.
  CPC .............. *B32B 5/022* (2013.01); *B32B 5/06* (2013.01); *B32B 5/08* (2013.01); *B32B 5/26* (2013.01); *B32B 7/12* (2013.01); *B32B 21/10* (2013.01); *C08F 220/06* (2013.01); *C09J 4/00* (2013.01); *A61F 2013/53035* (2013.01); *A61F 2013/530182* (2013.01); *A61F 2013/530189* (2013.01); *A61F 2013/530233* (2013.01); *A61F 2013/530306* (2013.01); *A61F 2013/530343* (2013.01); *A61F 2013/530372* (2013.01); *A61F 2013/530437* (2013.01); *A61F 2013/530496* (2013.01); *B32B 2250/02* (2013.01); *B32B 2250/03* (2013.01); *B32B 2250/20* (2013.01); *B32B 2255/02* (2013.01); *B32B 2255/26* (2013.01); *B32B 2262/02* (2013.01); *B32B 2262/0253* (2013.01); *B32B 2262/0276* (2013.01); *B32B 2262/0284* (2013.01); *B32B 2262/062* (2013.01); *B32B 2262/065* (2013.01); *B32B 2262/067* (2013.01); *B32B 2262/14* (2013.01); *B32B 2264/02* (2013.01); *B32B 2264/025* (2013.01); *B32B 2264/0228* (2013.01); *B32B 2264/0264* (2013.01); *B32B 2264/062* (2013.01); *B32B 2307/56* (2013.01); *B32B 2307/7163* (2013.01); *B32B 2307/72* (2013.01); *B32B 2307/726* (2013.01); *B32B 2307/732* (2013.01); *B32B 2410/00* (2013.01)

(56) References Cited

U.S. PATENT DOCUMENTS

| | | | | |
|---|---|---|---|---|
| 5,432,215 A | * | 7/1995 | Girg | C04B 28/02 524/28 |
| 5,773,542 A | * | 6/1998 | Koudate | C08F 2/32 526/215 |
| 5,821,179 A | * | 10/1998 | Masaki | A61F 13/15203 442/375 |
| 6,194,630 B1 | * | 2/2001 | Chihani | D06M 23/08 604/366 |
| 6,686,414 B1 | | 2/2004 | Anderson et al. | |
| 2003/0186612 A1 | | 10/2003 | Goldwasser et al. | |
| 2005/0028441 A1 | | 2/2005 | Abitz et al. | |
| 2006/0147689 A1 | * | 7/2006 | Wallajapet | A61L 15/26 428/292.1 |
| 2008/0190576 A1 | * | 8/2008 | Champ | D21H 23/16 162/164.1 |
| 2011/0232188 A1 | * | 9/2011 | Kennedy | A01G 24/48 47/59 S |
| 2014/0051813 A1 | * | 2/2014 | Won | C08J 3/245 525/384 |
| 2014/0230322 A1 | * | 8/2014 | Zhang | C05F 3/04 47/32.8 |

FOREIGN PATENT DOCUMENTS

| | | |
|---|---|---|
| EP | 1 522 545 A1 | 4/2005 |
| EP | 1 548 179 A1 | 6/2005 |
| EP | 2 671 554 A1 | 12/2013 |
| WO | 9209193 A1 | 6/1992 |
| WO | 2012 024217 A1 | 2/2012 |
| WO | 2012 164044 A1 | 12/2012 |
| WO | 2012164044 A1 | 12/2012 |

OTHER PUBLICATIONS

WAM Netherlands, Moneymarkers Project, "Make a wish possible", Mar. 31, 2015, pp. 1-79, Canisius College, WAM.

Rabobank Dichterbij Westelijke Mijnstreek Herfst: Idee met groen randje EUREKA, Autumn 2015, pp. 1-40.

Declaration of author T.K.R. Jeuken for public availability of 'WAM Netherlands, Moneymarkers Project, "Make a wish possible"', Feb. 2, 2020.

Declaration of receiver A. Salur for public availability of 'WAM Netherlands, Moneymarkers Project, "Make a wish possible"', Feb. 20, 2020.

* cited by examiner

LAYERED PRODUCT COMPRISING SUPERABSORBENT POLYMER

FIELD OF THE INVENTION

The invention is directed to a layered product comprising a superabsorbent polymer (SAP), to a process for the preparation of the layered product and to the use of the layered product in horticulture or for transportation of plants.

BACKGROUND OF THE INVENTION

Superabsorbent polymers (SAP) are polymers that can absorb and retain extremely large amounts of water relative to their own mass. SAP particles, also called hydrogels, absorb water through hydrogel bonding with water molecules. SAP particles can absorb up to 500 times their weight; which is from 30-60 times their own volume of water. When the SAP particles absorb water they swell and their volume increases. SAP particles may slowly release the water after absorption.

It is well-known to use SAP particles for diapers and other sanitary products to improve the moisture absorption. Diapers made of layered products comprising SAP particles are known and described for example in EP1548179.

It is also known to use SAP particles mixed with soil for plant growth.

Explants are conventionally rooted, and seeds germinated, in liquid growth media or solid media that are liquid media gelled with agar. It takes a longer time for seeds germinated and explants rooted in these media to grow into bigger plants. The use of liquid or gelled media create ideal conditions, designed to encourage rapid growth of explants and seedlings, but they also stimulate a typical development of the roots. The use of liquid or gelled media results in plantlets developing roots with a different root epidermis with lesser root hairs, so called 'water roots'. When transferred to soil or other substrates these plantlets first need to develop 'ground roots', with more root hairs to improve the efficiency of water and mineral nutrients uptake from soil. This adaptation of their roots takes about a week, meaning that there is at least a week of growth delay.

SUMMARY OF THE INVENTION

It is an object of the invention to develop a plant growth medium in which the above-mentioned disadvantages do not occur.

The present invention provides a layered product comprising at least one natural fiber layer comprising a web of natural fibers and at least one SAP layer comprising a non-woven substrate comprising thermoplastic polymer fibers and a superabsorbent polymer adhered to the thermoplastic polymer fibers, wherein the non-woven substrate is a high loft fabric, for example a carded or an air-laid or spunlaid non-woven, and wherein the at least one natural fiber layer and the at least one SAP layer are connected to each other by needle punching, stitch bonding or using an adhesive.

In a first embodiment of the layered product according to the invention, the number of the natural fiber layer in the layered product is one, the number of the SAP layer in the layered product is one and the SAP layer comprises a single non-woven substrate comprising SAP-polymer.

Accordingly, the first embodiment of the layered product relates to a layered product comprising one natural fiber layer comprising a web of natural fibers and one SAP layer comprising one non-woven substrate comprising thermoplastic polymer fibers and a superabsorbent polymer adhered to the thermoplastic polymer fibers, wherein the non-woven substrate is a high loft fabric, for example a carded or an airlaid or spunlaid non-woven and, wherein the natural fiber layer and the SAP layer are connected to each other by needle punching, stitch bonding or using an adhesive.

The first embodiment can be used, for example, for the germination of seeds or the micropropagation of stock plant material. The first embodiment can further be used for the transportation of plants. In particular, the first embodiment can be used in dry form as a water absorbent material and in wet form to prevent dehydration of the plants during transportation of plants. Further, the layered product can act as a shock absorber. In some cases, the layered product of the first embodiment is folded such that the SAP layer is an inner layer. Such folded product is suitable for placing seeds or explants in the inner layer.

In a second embodiment, the number of the natural fiber layer in the layered product is at least two, the SAP layer (or each of the SAP layers when the layered product comprises more than one SAP layers) is between the natural fiber layers and the SAP layer (or each of the SAP layers when the layered product comprises more than one SAP layers) comprises one or more non-woven flat pieces of substrate comprising SAP particles. The SAP pieces are preferably evenly distributed over the surfaces of the adjacent natural fiber layers.

Accordingly, the second embodiment of the layered product relates to a layered product comprising at least two natural fiber layers each comprising a web of natural fibers and At least one SAP layer, wherein the SAP layer or each of the SAP layers is between two natural fiber layers, the SAP layer or each of the SAP layers comprises one or more non-woven substrates distributed over the surfaces of the adjacent natural fiber layers, wherein the non-woven substrate comprises thermoplastic polymer fibers and a superabsorbent polymer adhered to the thermoplastic polymer fibers, wherein the non-woven substrate is a high loft fabric, for example a carded or an airlaid or spunlaid non-woven, and wherein the at least two natural fiber layers and the at least one SAP layer are connected to each other by needle punching, stitch bonding or using an adhesive.

The second embodiment can be used, for example, for rooting of plant cuttings, growth of plants, or for watering and irrigation management of plants.

BRIEF DESCRIPTION OF THE DRAWINGS

The invention is hereinafter described referring to the drawings.

In FIG. 1, the layered product comprises one natural fiber layer 10 and one SAP layer 20, which are both in the form of a continuous sheet. The natural fiber layer 10 and the SAP layer 20 are connected to each other by fibers 30, made by needle punching. The layered product may be folded such that the SAP layer 20 becomes the inner layer, as indicated by an arrow. A U-shaped product is thus obtained, which is suitable for placing e.g. seeds and explants therein.

In FIG. 2, the layered product comprises three natural fiber layers 10 and two SAP layers 20. The SAP layers 20 are situated between the adjacent natural fiber layers 10. The natural fiber layers 10 are in the form of a continuous sheet. Each of the SAP layers consist of a plurality of flat pieces distributed over the faces of the natural fiber layers 10 with a space 21 between the flat pieces. The natural fiber layers 10 and the SAP layers 20 are connected to each other by fibers 30, made by needle punching. In this embodiment, folding of the layered product as indicated by the arrow results in a U-shaped product wherein the natural fiber layer is the inner layer.

DETAILED DESCRIPTION OF THE INVENTION

Figure 1:
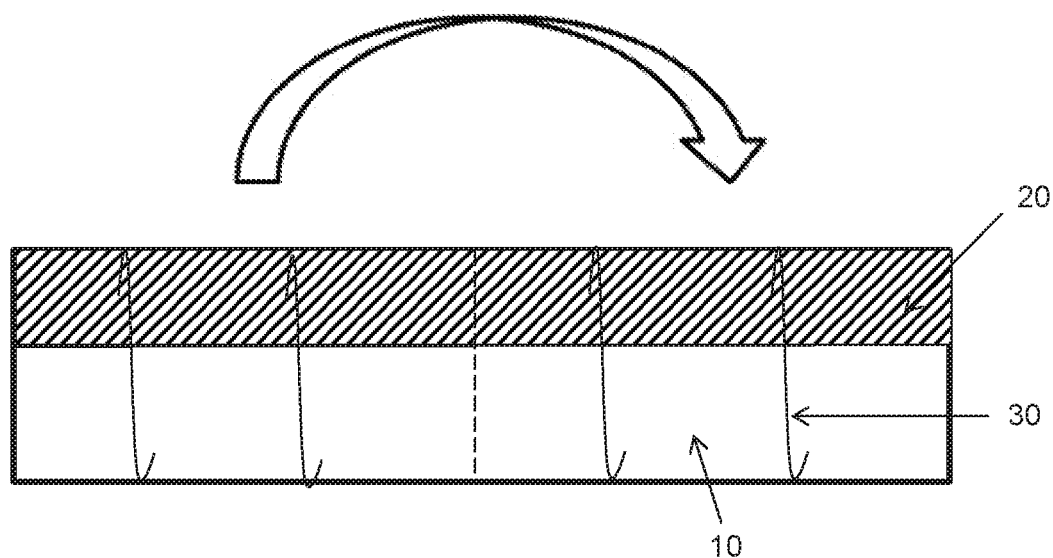
FIG. 1 schematically illustrates an example of the first embodiment of the layered product of the invention.
Figure 2:
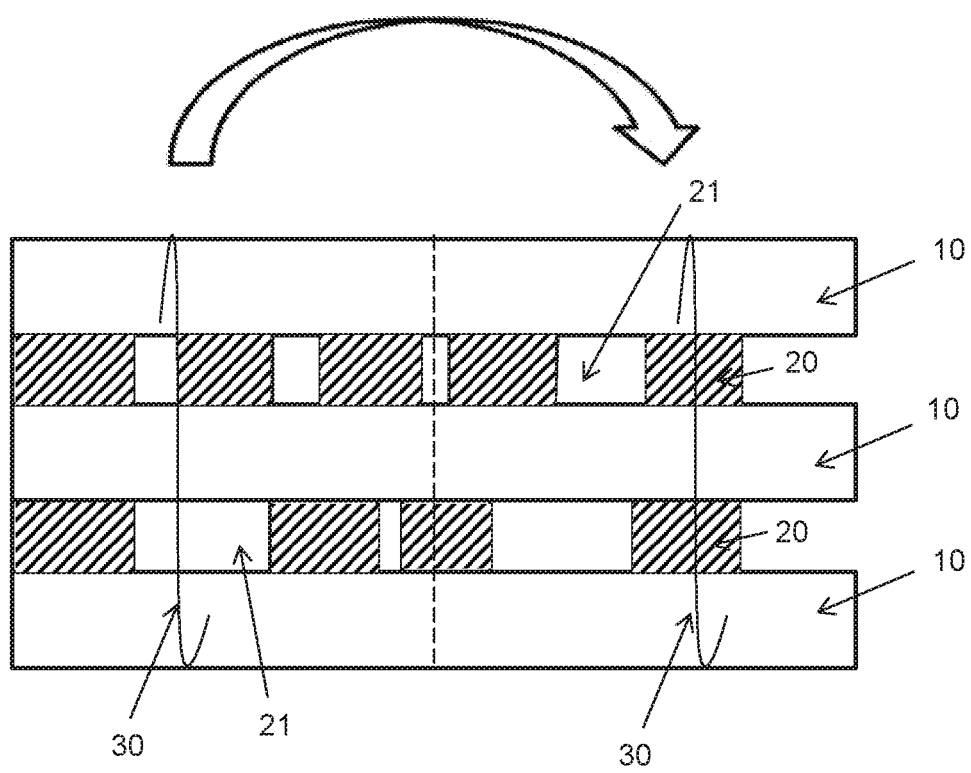
FIG. 2 schematically illustrates an example of the second embodiment of the layered product of the invention.
Figure 3:
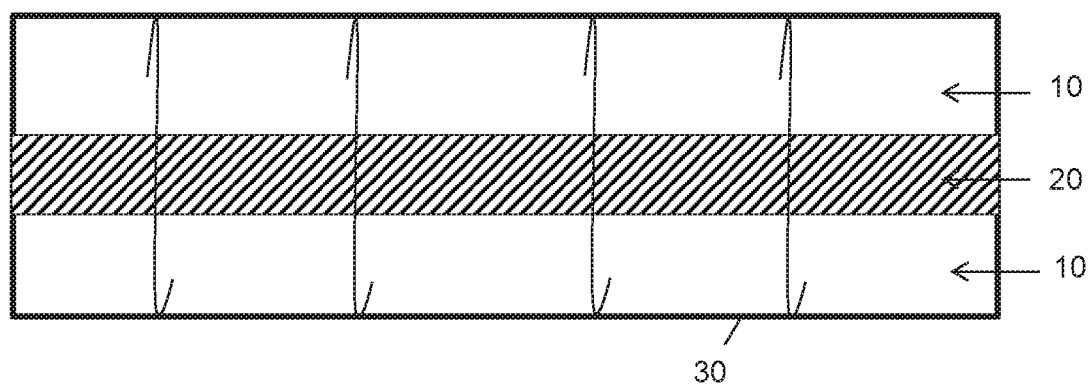
FIG. 3 shows an example wherein one SAP containing layer 20 is embedded between two layers of natural fibers 10. The layers are connected to each other by needle punching or stitching.

It has surprisingly been discovered by the inventors that explants form ground roots when they are rooted in the layered product of the invention. This means that when the small plants are replanted in soil or other substrates less growth delay occurs and the plant can grow further more rapidly. This considerably improves the productivity for the grower.

The natural fiber layer gives a structure to the layered product and the SAP in the SAP layer retains water and dissolved mineral nutrients and provides a source thereof for the uptake by explants, benefitting their growth and the development of roots. Due to the porous structure of the natural fiber layer and the SAP layer, roots can grow through the whole volume of the layered product.

By needle punching the natural fibers in the natural fiber layer are mechanically bonded by interlocking to form a non-woven fabric. When this is done in presence of the SAP layer (or each of the SAP layers when the layered product comprises more than one SAP layers) the fibers also entangle with the fibers in the SAP layer (or each of the SAP layers when the layered product comprises more than one SAP layers), which fix the layers together. When the natural fiber layer is premanufactured it can be affixed to the SAP layer by stitch bonding or by using an adhesive.

The natural fibers in the natural fiber layer create entanglements with the fibers in the SAP layer, which fix the layers together. The needle punching and stitch bonding further bonds together the natural fibers in the natural fiber layer.

The layered product should have a sufficient strength for integrity while maintaining sufficient space for the growth of roots. The skilled person can adjust the density of the stitches in the layered product to obtain the desired strength of the product and space for the growth of the roots.

Preferably, the layers of the layered product are interconnected by needle punching or stitching, preferably by needle punching.

The following description applies to both the first embodiment and the second embodiment, unless stated otherwise.

Natural Fiber Layer

The web of the natural fibers is made by intermixing natural fibers. The intermixing of natural fibers may be done e.g. by a carding process.

The natural fiber layer comprises loosely intermixed natural fibers. Preferably, the natural fiber layer substantially consists of loosely intermixed natural fibers. Preferably, the natural fiber layer comprises less than 5 wt % of a thermoplastic polymer, more preferably less than 1 wt % of a thermoplastic polymer, more preferably does not comprise a thermoplastic polymer.

Preferably, the natural fibers have an average length of 2-15 cm, more preferably between 2 and 10 cm, or between 3 and 7 cm.

Preferably, the natural fibers are selected from the group consisting of hemp, jute, flax, coir, cotton and wood fibers. This is advantageous in that the layers are biodegradable.

Preferably, the natural fiber layer (or each of the natural fiber layers when there are two or more layers) has an average density of 12.5-75 g/L.

SAP Layer

The SAP layer comprises a non-woven substrate comprising thermoplastic polymer fibers. The non-woven substrate is a high loft fabric, for example a carded or an airlaid or spunlaid non-woven. When the non-woven substrate is a spunlaid non-woven, the non-woven substrate is made of thermoplastic polymer fibers which are bonded by a partial melting of the thermoplastic polymer fibers. When the non-woven substrate is a carded or an air-laid non-woven, the non-woven substrate further can comprise cellulosic fibers and the thermoplastic polymer fibers and the cellulosic fibers are bonded by a partial melting of the thermoplastic polymer fibers.

The SAP layer further comprises SAP adhered as particles to the thermoplastic polymer fibers (and to the cellulosic fibers when present) in the non-woven substrate. The SAP particles can expand within the substrate when exposed to moisture, due to the high loft character of the substrate.

As also described elsewhere, preferably, monomers for forming the SAP are applied to the non-woven substrate in a liquid form and the monomers are polymerized to form SAP particles attached to the thermoplastic polymer fibers and any cellulosic fibers.

Cellulosic fibers are naturally occurring fibers containing cellulose, like for example jute, hemp, flax, coir, cotton, and wood fibers and the like.

The SAP layer can be present in different forms. Examples of suitable forms are a sheet, or flat pieces like for example scraps, flakes and the like.

Preferably, the sheet or the flat pieces of the SAP layer have an average density of 25-85 g/L in a dry state.

Preferably, the amount of the SAP in the SAP layer is 5-90 wt %, more preferably 5-70 wt %, 5-65 wt %, 5-60 wt %, 10-60 wt %, 20-60 wt % or 30-60 wt %, based on the weight of the SAP layer (non-woven substrates and SAP) in a dry state.

When the SAP layer is in the form of a sheet, the dimension of the SAP layer (which is the dimension of the non-woven substrate which contains the SAP polymer) may be similar to the dimension of the natural fiber layer (which is the dimension of web of the natural fibers). Preferably, the SAP layer has an area which is 90-110%, preferably 95-105%, of the area of the natural fiber layer.

The thickness of the sheet or flat pieces typically ranges between 0.5 and 10 mm, preferably between 1 and 5 mm.

When the SAP layer comprises at least two or more flat pieces, these pieces are preferably distributed over the surfaces of the natural fiber layers. The pieces have a generally flat shape and their surfaces have smaller area than the natural fiber layer.

When the SAP layer has at least two or more flat pieces, said pieces may typically have a dimension between 5 mm*5 mm*0.5 mm and 20 mm*20 mm*10 mm, more typically between 10 mm*10 mm*1 mm and 20 mm*20 mm*4 mm. Typically, the SAP layer has at least 10 flat pieces. Typically, the number of flat pieces in one SAP layer is 30-400, preferably 40-370, per $m^2$ of the SAP layer.

The thermoplastic polymer in the SAP layer may be any polymer or combination of polymers suitable for the purpose of bonding the fibers to form a desired shape. Suitable examples of the thermoplastic polymer include polylactic acid, polyethylene terephthalate, polyethylene and polypropylene and mixtures of these. Preferably, the thermoplastic polymer comprises polyactic acid due to its biodegradability.

There are many types of super absorbent polymers (SAP) that can be used in the present invention. A commonly used SAP is a sodium or potassium salt of polyacrylic acid. Other materials that are super absorbent polymers are, for example, copolymers of acrylic acid with acrylamide, ethylene maleic anhydride copolymers, crosslinked carboxymethyl cellulose, polyvinyl alcohol copolymers, crosslinked polyethylene oxide and starch grafted copolymers of polyacrylonitrile.

According to a preferred embodiment of the invention the SAPs are prepared by polymerizing: a first monomer containing an acrylic acid group with the formula $H_2C=CR_1R_2$, wherein $R_1=H$ or an alkyl group with 1-10 carbon atoms, and $R_2=COOH$, and a second monomer which is a compound selected from: a monomer containing an acrylic acid group and having the formula $H_2C=CR_3R_4$, wherein $R_3=H$ or an alkyl group with 1-10 carbon atoms and $R_4$ is an alkyl carboxyl group with 1-10 carbon atoms and not equal to $R_2$; a monomer containing an acrylamide group and having the formula $H_2C=CR_3CONHR_5$, wherein $R_3$ is as defined above and $R_5$ is an alkyl group with 1-10 carbon atoms; a compound selected from the group consisting of N,N dimethyl acrylamide, diacetone acrylamide, methoxy (polyethylene glycol)-methacrylate, ammonium sulphate ethyl methacrylate, vinyl acetate, N-vinyl-2-pyrrolidone, N-vinyl-N-methylacetamide, vinyl cyanide, crotonic acid, 3-amino-crotonamide, 4-hydroxybutyl acrylate, 4-hydroxybutyl methacrylate, hydroxypropyl acrylate, hydroxypropyl methacrylate, hydroxyethyl acrylate and hydroxyethyl methacrylate, under the influence of actinic radiation in the presence of a photoinitiator.

Preferably, the first monomer is neutralized with an inorganic base before polymerization.

These preferred SAPs are described in patent publication EP-B-1522545 which is incorporated herein by reference.

Layered Product

In the layered product of the invention, the natural fiber layer and the SAP layer are preferably placed in a face-to-face contact with each other.

Preferably, the layered product has a density of 15-100 g/L in a dry state.

Preferably, the amount of the SAP layer (for example in the form of a sheet or flat pieces) in the layered product is 1-30 wt %, preferably 3-20 wt %, more preferably 4-10 wt %, of the layered product in a dry state.

In the second embodiment, the total number of the natural fiber layers and the SAP layers in the layered product of the invention can be preferably at least 15, at least 20 or 25 and/or at most 40 or at most 35, when the SAP layer is present as flat pieces in spaces between adjacent natural fiber layers. There may be one or more spaces between adjacent natural fiber layers which do not comprise the SAP layer. In case the SAP layer is a sheet, the total number of layers of the layered product can be between 3 and 20, preferably between 3 and 10.

Process for Making the Layered Product

The invention also provides a process for making the layered product according to the invention.

Preferably, the process for making the layered product according to the invention comprises the steps of:
a) providing the SAP layer,
b) placing the natural fiber layer and the SAP layer in contact with each other in a face-to-face arrangement and
c) connecting the layers by needle punching, stitch bonding or using an adhesive.

Preferably, step a) involves
a1) providing droplets of a mixture of at least one monomer and at least one initiator on the non-woven substrate and
a2) radiating or heating the droplets to polymerize the at least one monomer.

The at least one monomer can, for example, be chosen from monomers containing an acrylic acid group, an acrylamide group, an acrylate group, a methacrylate group, a maleic anhydride group, an acrylonitrile group, an ethylene oxide group or a vinyl alcohol group. Also mixtures of these monomers can be used. During polymerization of a monomer mixture copolymers will form.

For the second embodiment, step a) may further comprise
a3) reducing the size of the non-woven substrate to obtain the non-woven substrates having a dimension between 5 mm*5 mm*0.5 mm and 20 mm*20 mm*4 mm.

For the second embodiment, steps b) and c) of the process may involve the use of a cross-lapper to form the multilayer structure.

Use of the Product

The invention further relates to use of the layered product of the invention in horticulture. In particular, the invention relates to use of the layered product of the invention for the germination of seeds, micropropagation of stock plant material, rooting of plant cuttings, growth of plants, watering or irrigation management of plants.

For use of the layered product of the invention for the germination of seeds or micropropagation of plants and trees, the layered product of the invention is preferably of the first embodiment described above, i.e. the number of the natural fiber layer is one, the number of the SAP layer is one and the SAP layer is in the form of the sheet. Alternatively the second embodiment where the SAP layer is in the form of a sheet between two natural fiber layers is also very well suited for this application.

For use of the layered product of the invention for rooting of plant cuttings, growth of plants, watering or irrigation management of plants, the layered product of the invention is preferably of the second embodiment described above, i.e. the number of the natural fiber layer is at least two and the SAP layer is between two natural fiber layers and the SAP layer is in the form of a sheet or the flat pieces.

The invention further relates to use of the layered product of the invention in transportation of plants. In particular, the invention relates to use of the layered product of the invention for absorbing water during transportation or prevention of dehydration of plants during transportation.

For use of the layered product of the invention for absorbing water during transportation and prevention of dehydration of plants during transportation, the layered product of the invention is preferably of the first embodiment described above, i.e. the number of the natural fiber layer is one, the number of the SAP layer is one and the SAP layer is in the form of the sheet.

The invention further provides a plant plug comprising a plant and the layered product of the invention.

In some embodiments, the first embodiment of the layered product of the invention may be used to obtain a plant plug comprising a seedling or an explant and the plant plug may be placed in the second embodiment of the layered product for the further growth of the seedling or plantling.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps. The process consisting of these steps may be advantageous in that it offers a simpler, more economical process.

What is claimed is:

1. A layered product for use in horticulture, comprising:
   at least one natural fiber layer comprising a web of natural fibers and
   at least one SAP layer comprising a non-woven substrate comprising a thermoplastic polymer fibers and a superabsorbent polymer adhered to the thermoplastic polymer fibers,
   wherein the non-woven substrate is a carded, an airlaid or spunlaid non-woven,
   wherein the at least one SAP layer is in the form of a sheet,
   wherein the thermoplastic polymer in the at least one SAP layer comprises a polylactic acid,
   wherein the natural fibers are selected from the group consisting of hemp, jute, flax, coir, cotton and wood fibers,
   wherein the natural fibers have an average length of 2-15 cm,
   wherein the at least one natural fiber layer has an average density of 12.5-75 g/L,
   wherein the at least one natural fiber layer comprises less than 5 wt. % of a thermoplastic polymer, and wherein the at least one natural fiber layer and the at least one SAP layer are connected to each other by needle punching, wherein the layered product has the at least one natural fiber on one side and the at least one SAP layer on an opposite side.

2. The layered product according to claim 1, wherein the number of the at least one natural fiber layer in the layered product is one, the number of the at least one SAP layers in the layered product is one and the SAP layer comprises a single non-woven substrate comprising SAP-polymer, and wherein the at least one SAP layer has an area which is 90-110% of the area of the natural fiber layer.

3. The layered product according to claim 1, wherein the amount of the SAP in the at least one SAP layer is 5-60 wt. % based on the total weight of the non-woven substrates and the SAP in a dry state.

4. The layered product according to claim 1, the amount of the non-woven substrate in the at least one SAP layer in the layered product is 1-30 wt. % of the layered product in a dry state.

5. The layered product according to claim 1, wherein the SAP is prepared by polymerizing:
   a first monomer containing an acrylic acid group with the formula $H_2C=CR_1R_2$, wherein $R_1$=H or an alkyl group with 1-10 carbon atoms, and $R_2$=COOH, and
   a second monomer which is a compound selected from:
   a monomer containing an acrylic acid group and having the formula $H_2C=CR_3R_4$, wherein $R_3$=H or an alkyl group with 1-10 carbon atoms and $R_4$ is an alkyl carboxyl group with 1-10 carbon atoms and not equal to $R_2$;
   a monomer containing an acrylamide group and having the formula $H_2C=CR_3CONHR_5$, wherein $R_3$ is as defined above and $R_5$ is an alkyl group with 1-10 carbon atoms;
   a compound selected from the group consisting of N,N dimethyl acrylamide, diacetone acrylamide, methoxy (polyethylene glycol)-methacrylate, ammonium sulphate ethyl methacrylate, vinyl acetate, N-vinyl-2-pyrrolidone, N-vinyl-N-methylacetamide, vinyl cyanide, crotonic acid, 3-amino-crotonamide, 4-hydroxybutyl acrylate, 4-hydroxybutyl methacrylate, hydroxypropyl acrylate, hydroxypropyl methacrylate, hydroxyethyl acrylate and hydroxyethyl methacrylate,
   under the influence of actinic radiation in the presence of a photoinitiator.

6. The layered product according to claim 5, wherein the first monomer is neutralized with an inorganic base before polymerization.

7. The layered product according to claim 2, wherein the at least one SAP layer has an area which is 95-105% of the area of the natural fiber layer.

8. The layered product according to claim 1, wherein the at least one natural fiber layer comprises less than 1 wt. % of a thermoplastic polymer, wherein the amount of the non-woven substrate in the at least one SAP layer in the layered product is 3-20 wt. % of the layered product in a dry state.

9. The layered product according to claim 8, wherein the at least one natural fiber layer does not comprise the thermoplastic polymer, wherein the amount of the non-woven substrate in the at least one SAP layer in the layered product is 4-10 wt. % of the layered product in a dry state.

10. A process for the preparation of the layered product according to claim 1, wherein the process comprises the steps of:
    a) providing the at least one SAP layer in the form of a continuous sheet,
    b) placing the at least one natural fiber layer and the at least one SAP layer in contact with each other and
    c) connecting the at least one natural fiber layer and the at least one SAP layer by needle punching.

11. The process according to claim 10, wherein step a) involves
    a1) providing droplets of a mixture of at least one monomer and at least one initiator on the non-woven substrate and
    a2) radiating or heating the droplets to polymerize the at least one monomer.

12. A method, comprising the steps of: obtaining the layered product according to claim 1, and using the layered product for the germination of seeds, micropropagation of stock plant material, rooting of plant cuttings, growth of plants, watering or irrigation management of plants.

13. A method, comprising the steps of: obtaining the layered product according to claim 1, and using the layered product for absorbing water during transportation or prevention of dehydration of plants during transportation.

* * * * *